United States Patent [19]

Sakata et al.

[11] Patent Number: 4,547,463

[45] Date of Patent: Oct. 15, 1985

[54] METHOD OF IMMOBILIZING MICROORGANISMS

[75] Inventors: Co Sakata, Kawasaki; Hirosuke Imai, Yokohama, both of Japan

[73] Assignee: Nippon Oil Company, Ltd., Japan

[21] Appl. No.: 379,319

[22] Filed: May 18, 1982

[30] Foreign Application Priority Data

May 18, 1981 [JP] Japan ................................ 56-73438

[51] Int. Cl.$^4$ ............................................ C12N 11/08
[52] U.S. Cl. ...................................... 435/180; 525/8;
525/242; 526/287
[58] Field of Search ......................................... 435/180

[56] References Cited

U.S. PATENT DOCUMENTS 4,148,689  4/1979  Hino ..................... 435/180
4,240,889 12/1980  Yoda ..................... 435/180
4,263,400  4/1981  Ushiro ................... 435/177
4,276,381  6/1981  Sakimae ................. 435/180

Primary Examiner—Christopher A. Henderson
Attorney, Agent, or Firm—McGlew and Tuttle

[57] ABSTRACT

A method of immobilizing microorganisms which comprises the steps of bringing a suspension of living cells of a microorganism into contact with a water-insoluble copolymer containing structural units derived from 2-acrylamidoethanesulfonic acid or a derivative thereof to cause the microorganism to become adsorbed on the copolymer, and bringing the water-insoluble copolymer having the microorganism adsorbed thereon into contact with a nutrient medium for the cultivation of the microorganism to increase the number of cells present on the copolymer.

10 Claims, No Drawings

METHOD OF IMMOBILIZING MICROORGANISMS

BACKGROUND OF THE INVENTION

1. Field of the Invention

This invention relates to the immobilization of microorganisms. More particularly, it relates to a method of immobilizing microorganisms in which living cells of a microorganism are adsorbed on a water-insoluble polymeric carrier and then grown.

2. Description of the Prior Art

In recent years, many attempts have been made to produce useful substances through enzyme reactions using so-called immobilized microorganisms (i.e., an immobilized form of microorganisms having an enzyme activity). The use of immobilized microorganisms has a great advantage in that the enzyme reactions can be carried out in a continuous manner.

The currently known techniques for immobilizing microorganisms in a viable state include:

(1) the method of entrapping microbial cells in the matrix of a polymer gel;
(2) the method of causing microbial cells to be ionically or physically adsorbed on a water-insoluble carrier;
(3) the method of coating microbial cells with a polymer film having semipermeability;

and the like.

Among them, the method (1) of entrapping microbial cells in the matrix of a polymer gel has been investigated to a full extent. By way of example, immobilized microorganism gel beads can be prepared either by suspending microbial cells in an aqueous solution of sodium alginate and then adding the resulting suspension dropwise to an aqueous solution of calcium chloride, or by suspending microbial cells in an aqueous solution of κ-carrageenin and then adding the resulting suspension in an aqueous solution of potassium chloride. Moreover, a mass of immobilized microorganism gel can be prepared by adding acrylamide, N,N'-methylenebisacrylamide, and a polymerization initiator to a suspension of microbial cells and then polymerizing the resulting mixture. These immobilized microorganism gels are characterized in that the catalytic activity for inherent enzyme reactions can be remarkably enhanced by passing a nutrient medium for the cultivation of the microorganism through the gel and thus increasing the number of microbial cells present therein. Although the aforesaid gelation procedures can be aseptically performed on a laboratory scale, very complicated and uneconomical operations are required when they are carried out in large-scale industrial equipment. Moreover, the resulting immobilized microorganism gel may be contaminated with miscellaneous microorganisms, so that undesired enzyme reactions take place concurrently to impair the purity of the desired useful product.

In the method (2) of causing microbial cells to be ionically or physically adsorbed on a water-insoluble carrier, various materials such as clay, silica gel, ion exchange resins, and the like are known to be suitable for use as the carrier. However, this method suffers from the disadvantage that the number of microbial cells adsorbed on the carrier is rather small. Even after the microorganism is grown by passing a nutrient medium through the carrier, the cell concentration is lower than that achieved by the method (1). Nevertheless, the method (2) has the advantage of permitting microorganisms to be aseptically immobilized with comparative ease in industrial equipment.

The method (3) of coating microbial cells with a polymer film having semipermeability is the so-called microencapsulation method. From an industrial point of view, this method is not satisfactory because the microbial cells may be inactivated by the organic solvent or monomer used for the formation of a film and because the complicated procedure for the preparation of microcapsules makes this method expensive.

As described above, the well-known techniques for immobilizing microorganisms can exhibit their advantages in case of enzyme reactions on a small scale. However, when they are utilized on an industrial scale, their disadvantages are so great that it may often be more economical to use free (i.e., not immobilized) microorganisms according to conventional procedure.

SUMMARY OF THE INVENTION

It is an object of the present invention to provide a method of immobilizing microorganisms which permits attainment of high enzyme activities.

It is another object of the present invention to provide a method of immobilizing microorganisms which, even when carried out on an industrial scale, exhibits good operability and eliminates the possibility of contamination especially with miscellaneous microorganisms.

It is still another object of the present invention to provide a method of immobilizing microorganisms in which, even if only a small number of microbial cells are initially immobilized, they can be grown.

The above and other objects of the present invention are accomplished by a method of immobilizing microorganisms which comprises the steps of bringing a suspension of living cells of a microorganism into contact with a water-insoluble copolymer containing 10 to 99% by weight of structural units derived from 2-acrylamidoethanesulfonic acid or a derivative thereof to cause the microorganism to become adsorbed on the copolymer, and bringing the water-insoluble copolymer having the microorganism adsorbed thereon into contact with a nutrient medium for the cultivation of the microorganism to increase the number of cells present on the copolymer.

DETAILED DESCRIPTION OF THE PREFERRED EMBODIMENTS

The term "2-acrylamidoethanesulfonic acid or a derivative thereof (hereinafter referred to as AES)" is used herein to denote sulfonic acids of the general formula

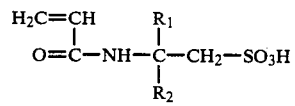

where $R_1$ and $R_2$ independently represent hydrogen atoms or hydrocarbon radicals having 1 to 12 carbon atoms, and metal salts of the foregoing acids. In these metal salts, no particular limitation is imposed on the type of metals present therein, and any metal that combines with common sulfonic acids to form their salts can be used. However, it is usually preferable to use alkali metals and alkaline earth metals.

Typical examples of the above-defined AES include 2-acrylamidoethanesulfonic acid (where $R_1$ and $R_2$ are hydrogen atoms), 2-acrylamidopropanesulfonic acid (where $R_1$ is a hydrogen atom and $R_2$ is a methyl radical), 2-acrylamido-2-methyl-propanesulfonic acid (where $R_1$ and $R_2$ are methyl radicals), and alkali metal or alkaline earth metal salts thereof. Among these compounds, 2-acrylamido-2-methyl-propanesulfonic acid is particularly preferred.

In the method of the present invention, a water-insoluble copolymer containing 10 to 99% by weight of structural units derived from the above-defined AES (hereinafter referred to as AES units) is used. The copolymers which are useful for this purpose are roughly divided into two categories: (a) copolymers obtained by the copolymerization of AES and one or more other comonomers and (b) graft polymers obtained by the graft polymerization of AES on natural or synthetic high-molecular compounds.

The comonomers which are used in preparing the former type of copolymers can be any monomers that copolymerize with AES in the presence of a free-radical initiator to form water-insoluble copolymers. Such monomers are typified by cross-linkable vinyl monomers having two or more carbon-to-carbon double bonds in the molecule, and specific examples thereof include N,N'-methylenebisacrylamide, N,N'-propylenebisacrylamide, N-acryloylacrylamide, diacrylamido dimethyl ether, 1,2-diacrylamido ethylene glycol, ethyleneureabisacrylamide, 1,3,5-triacryl-hexahydro-S-triazine, and the like.

Moreover, the strength and water-insolubility of the resulting copolymer can be enhanced by using, as comonomers, monoethylenic monomers of the general formula

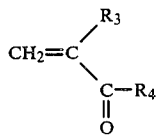

where $R_2$ represents a hydrogen atom, a methyl radical, or an ethyl radical, and $R_4$ represents an —OH group, an —$NH_2$ group, an —$NR_5R_6$ group (in which $R_5$ is a hydrogen atom or an alkyl radical having 1 to 20 carbon atoms and $R_6$ is an alkyl radical having 1 to 20 carbon atoms), an —$OR_7$ group (in which $R_7$ is an alkyl or hydroxyalkyl radical having 1 to 20 carbon atoms), or an aryl radical having 1 to 20 carbon atoms. Specific examples thereof include acrylic acid, methacrylic acid, acrylamide, and derivatives thereof; styrene, alkyl-substituted styrenes, acrylonitrile, methacrylonitrile, vinyl ethers, N-vinylpyrrolidone, vinyl acetate, maleic acid, and maleic anhydride; and the like. These monoethylenic monomers are preferably used in combination with a cross-linkable vinyl monomer as described above (e.g., in an amount of 0.1 to 10 times, preferably 0.5 to 5 times, the weight of the cross-linkable vinyl monomer).

Such AES copolymers can usually be prepared under any conditions that permit polymerization of the abovedescribed monomers. However, these monomers should generally be polymerized in the presence of a free-radical initiator. Although the reaction temperature may vary according to the type of free-radical initiator used, it usually ranges from −78° to 150° C. and preferably from 0° to 100° C. A variety of inert solvents can be used, but it is preferable to use solvents for AES (e.g., water, lower alcohols, dimethylformamide, and the like). Although the free-radical initiator can be any of common free-radical initiators used for radical polymerization, it is preferable to use a free-radical initiator soluble in the solvent. Typical examples of such free-radical initiators include hydrogen peroxide, potassium persulfate, ammonium persulfate, ketone peroxides, and the like.

Among various copolymers of AES and the abovedescribed comonomers, only copolymers containing 10 to 99% by weight, preferably 20 to 80% by weight, of AES units have the capacity of adsorbing microorganisms effectively and allowing them to grow. Copolymers containing AES units in an amount of less than 10% by weight have low adsorptive power for microorganisms and, moreover, do not allow the adsorbed microorganism to grow satisfactorily. On the other hand, homopolymers of AES are soluble in water and, therefore, can be used for the immobilization of microorganisms without further treatment only with difficulty.

Another type of water-insoluble copolymers containing AES units may also be used in the method of the present invention. Such copolymers can be prepared by introducing AES units into natural or synthetic high-molecular compounds through graft polymerization.

Typical examples of natural high-molecular compounds useful for this purpose include polysaccharides such as cellulose, cellulose acetate, cross-linked starch, alginic acid, agar, locust bean gum, carrageenin, etc.; polyamino acids; and the like. Typical examples of synthetic high-molecular compounds useful for this purpose include polystyrene and derivatives thereof; diene polymers such as polybutadiene, etc.; homopolymers of vinyl monomers such as polyvinyl alcohol, polyvinyl acetate, polyacrylamide, polyhydroxyethyl acrylate, polymethyl methacrylate, etc.; copolymers of vinyl monomers; and the like. These natural or synthetic high-molecular compounds may be used after being subjected to various treatments. By way of example, natural high-molecular compounds may be modified (as in carboxymethyl cellulose and methyl cellulose) by chemical procedures such as carboxymethylation, methylation, and the like, and synthetic high-molecular compounds may be cross-linked by physical means such as irradiation or by chemical means such as treatment with epichlorohydrin, formalin, or a dialdehyde.

The graft polymerization of AES on such a natural or synthetic high-molecular compound is effected by utilizing the conventional technique for the graft polymerization of a vinyl monomer on a high-molecular compound. More specifically, this technique involves the formation of a free radical in part of the molecule of the high-molecular compound, thus allowing the graft polymerization of AES to start from this active site. For this purpose, a redox catalyst or a radical-forming substance can usually be used as the initiator, for example, according to the procedure described in "Polymer Experimentation", Vol. 6 (Polymer Reactions), Kyoritsu Shuppan, September, 1978, pp. 153-154. Among others, it is preferable to use initiators such as ammonium persulfate, $Fe^{++}$—$H_2O_2$, ammonium cerium nitrate, and the like.

The amount of AES grafted on a natural or synthetic high-molecular compound should be such that the resulting graft polymer contains 10 to 99% by weight, preferably 20 to 80% by weight, of AES units. Where the natural or synthetic high-molecular compound on which AES was grafted is soluble in water, it is necessary to subject the graft polymer to a suitable treatment, such as cross-linking, for rendering it insoluble in water.

The water-insoluble copolymer used in the method of the present invention, which comprises either an AES copolymer or a natural or synthetic high-molecular compound having AES grafted thereon, usually swells in water. Accordingly, the copolymer is effectively used by swelling it in water prior to adsorption of a microorganism. The water content of the swollen copolymer (or water-containing gelatinous material) is generally in the range of 0.1 to 50 times, preferably 1 to 20 times, the weight of the copolymer. The AES units present in the copolymer may be in the form of either a sulfonic acid or a metal salt thereof. In this metal salt, any metal that has no adverse effect on the viability or growth of microorganisms can be used. Specific examples of such metals include lithium, sodium, potassium, calcium, magnesium, and the like.

In carrying out the present method of immobilizing microorganisms, a water-insoluble copolymer containing AES units is preliminarily formed into a suitable shape and then sterilized. This copolymer constitutes a water-insoluble polymeric carrier, on which living cells of a microorganism are adsorbed by bringing a suspension thereof into contact with the carrier. Thereafter, the water-insoluble polymeric carrier having the microorganism adsorbed thereon is brought into contact with a nutrient medium for the cultivation of the microorganism and placed under temperature and other environmental conditions suitable for the growth thereof, whereby the number of cells present on the copolymer is increased.

No particular limitation is imposed on the type of microorganism used in the method of the present invention, so long as it can yield useful substances through enzyme reactions. Specific examples of useful microorgnisms include bacteria, fungi, lichens, algae, protozoa, and the like.

In the method of the present invention, no particular limitation is imposed on the cell concentration of the microorganic suspension which is brought into contact with the water-insoluble polymeric carrier containing AES units. If the cell concentration of the microorganic suspension is low, the succeeding cultivation step requires a long period of time. On the contrary, the growth rate is increased by using a microorganic suspension with a high cell concentration, but an additional concentration step is required to prepare such a suspension.

No particular limitation is imposed on the length of the time during which a microorganic suspension is brought into contact with the water-insoluble polymeric carrier containing AES units. During this contact time, the microorganic suspension may be agitated or circulated so that the cells will be rapidly adsorbed on the water-insoluble polymeric carrier.

The step of growing the microorganism adsorbed on the water-insoluble polymeric carrier containing AES units is carried out by bringing the water-insoluble polymeric carrier into contact with a nutrient medium for the cultivation of the microorganism while maintaining environmental conditions (e.g., temperature, pH, aerobic or anaerobic atmosphere, and the like) suitable for the growth of the microorganism. In order to increase the growth rate of the microorganism, it is practicable to properly renew the nutrient medium in contact with the water-insoluble polymeric carrier having the microorganism adsorbed thereon or pass the nutrient medium continuously through a column packed with the water-insoluble polymeric carrier. Although the composition of the nutrient medium may vary slightly according to the type of microorganism used, any medium that is effective in promoting the growth of the microorganism can usually be used. Such a medium contains one or more carbon sources, nitrogen sources, minerals, and other nutrients.

Thus, according to the method of the present invention, a microorganism is immobilized by preparing a carrier for the immobilization thereof in advance, causing living cells of the microorganism to become adsorbed on the carrier, and then growing the adsorbed microorganism. Therefore, even when carried out on an industrial scale, the method of the present invention not only permits easy operation and positive prevention of contamination with miscellaneous microorganisms, but also can yield an immobilized microorganism preparation having a high cell density with good reproducibility.

The present invention is further illustrated by the following examples. Unless otherwise indicated, percentages are by weight.

EXAMPLE 1

An aqueous solution was prepared by dissolving 2.0 g of 2-acrylamido-2-methyl-propanesulfonic acid and 8.0 g of acrylamide in 90 g of water. After the addition of 1 g of N,N'-methylenebisacrylamide, this solution was kept at 30° C. Then, 5 ml of a 5% aqueous solution of tetramethylethylenediamine and 5 ml of a 2.5% aqueous solution of ammonium persulfate were added thereto, and this mixture was polymerized for 4 hours. A 30-g portion of the resulting copolymer gel was reduced to particles of 6-mesh or smaller size, packed into a column having an internal diameter of 3 cm and a height of 10 cm, washed with 300 ml of purified water, and then sterilized by heating at 120° C. for 10 minutes.

Next, a nutrient medium for the cultivation of yeasts containing 10% of glucose, 0.15% of yeast extract, 0.25% of ammonium chloride, 0.1% of sodium chloride, 0.55% of dipotassium phosphate, 0.012% of magnesium sulfate, 0.001% of calcium chloride, and 0.3% of citric acid was prepared and sterlized (by heating at 120° C. for 10 minutes). A 300-ml portion of this nutrient medium was inoculated with J.B.A. (Japan Brewer's Association) No. 6 yeast by dipping a yeast-loaded platinum loop into the medium and repeating this operation three times. Thereafter, the medium was shaken at 30° C. for 24 hours to form a yeast suspension.

While the column packed with the aforesaid copolymer gel was kept at 30° C., this yeast suspension was passed therethrough from the bottom at a flow rate of 8 ml/hr. The passage of the yeast suspension was discontinued after 24 hours, and a fresh nutrient medium having the same composition was passed through the column at a flow rate of 80 ml/hr. On the basis of the ethanol concentration of the column effluent obtained after 3 days, the density of the immobilized yeast cells was estimated to be $7 \times 10^8$ cells per gram of the copolymer gel.

EXAMPLE 2

To 100 g of a 10% aqueous solution of 2-acrylamido-2-methyl-propanesulfonic acid was added 4 g of N,N'-methylenebisacrylamide, followed by 1 ml of a 1% aqueous solution of hydrogen peroxide and 5 ml of a 0.5% aqueous solution of ferrous sulfate. This mixture was polymerized at 40° C. for 4 hours to form a water-insoluble copolymer. The resulting copolymer gel was reduced to particles of 6-mesh or smaller size. A 20-g portion of the gel was placed in a 100-ml Erlenmeyer flask, washed three times with 50-ml portions of purified water, and then sterilized.

The same nutrient medium as used in Example 1 was inoculated with J.B.A. No. 6 yeast by dipping a yeast-loaded platinum loop in the medium, and then shaken at 30° C. for 24 hours. A 30-ml portion of the resulting yeast suspension was added to the aforesaid 100-ml flask, which was allowed to stand at 30° C. for 48 hours. After removal of the yeast suspension, the gel was washed three times with purified and sterilized water. Then, 30 ml of a fresh nutrient medium having the same composition was added to the flask, which was kept at 30° C. On the basis of the ethanol concentration of the flask contents obtained after 4 hours, the density of the immobilized yeast cells was estimated to be $10^9$ cells per gram of the copolymer.

On microscopic examination of cross sections of some copolymer particles, colonies of the yeast were found not only on the surface of the copolymer particles but also in their internal regions adjacent to the surface.

EXAMPLE 3

A gel was synthesized in the same manner as described in Example 2, and reduced to particles of 6-mesh or smaller size. A 20-g portion of the gel was packed into a 50-ml column and sterilized. While this column was kept at 30° C., the same yeast suspension as described in Example 2 was passed therethrough at a flow rate of 8 ml/hr. After 24 hours, the yeast suspension was replaced by the same nutrient medium as used in Example 1, which was passed through the column at a flow rate of 80 ml/hr for the purpose of ethanol production. On the basis of the ethanol concentration of the column effluent obtained after 24 hours, the density of the immobilized yeast cells was estimated to be $5 \times 10^9$ cells per gram of the copolymer.

EXAMPLE 4

To 100 g of a 15% aqueous solution of 2-acrylamido-2-methyl-propanesulfonic acid was added 1 g of N,N'-propylenebisacrylamide, followed by 5 ml of a 2.5% aqueous solution of ammonium persulfate and 5 ml of a 5% aqueous solution of tetramethylethylenediamine. This mixture was polymerized at 30° C. for 4 hours to form a water-insoluble copolymer. The resulting copolymer gel was reduced to particles of 6-mesh or smaller size. A 20-g portion of the gel was worked up in the same manner as described in Example 3. On the basis of the ethanol concentration of the column effluent, the density of the immobilized yeast cells was estimated to be $3 \times 10^9$ cells per gram of the copolymer.

After the passage of the nutrient medium was discontinued, a sterilized solution (pH=6) containing 10% of glucose and 0.012% of magnesium sulfate was passed through the column at a flow rate of 8 ml/hr for the purpose of ethanol production. The column effluent obtained after 24 hours had an ethanol concentration of 4.8%.

EXAMPLE 5

An aqueous solution was prepared by dissolving 7.4 g of 2-acrylamido-2-methyl-propanesulfonic acid and 2.6 g of acrylamide in 90 g of water. To this solution was added 1 g of N,N'-methylenebisacrylamide, followed by 1 ml of a 1% aqueous solution of hydrogen peroxide and 5 ml of a 0.5% aqueous solution of ferrous sulfate. This mixture was polymerized at 40° C. for 5 hours to form a water-insoluble copolymer. The resulting copolymer gel was reduced to particles of 6-mesh or smaller size and then worked up in the same manner as described in Example 3. On the basis of the ethanol concentration of the column effluent, the density of the immobilized yeast cells was estimated to be $5 \times 10^9$ cells per gram of the copolymer.

EXAMPLE 6

An aqueous solution was prepared by dissolving 7.1 g of 2-acrylamido-2-methyl-propanesulfonic acid and 2.9 g of hydroxyethylacrylate in 90 g of water. To this solution was added 1 g of N,N'-methylenebisacrylamide, followed by 5 ml of a 1% aqueous solution of hydrogen peroxide and 1 ml of a 0.5% aqueous solution of ferrous sulfate. This mixture was polymerized at 40° C. for 5 hours to form a water-insoluble copolymer. The resulting copolymer gel was reduced to particles of 6-mesh or smaller size. A 20-g portion of the gel was worked up in the same manner as described in Example 3. On the basis of the ethanol concentration of the column effluent, the density of the immobilized yeast cells was estimated to be $4 \times 10^9$ cells per gram of the copolymer.

EXAMPLE 7

An aqueous solution was prepared by dissolving 7.6 g of 2-acrylamido-2-methyl-propanesulfonic acid and 2.4 g of methacrylic acid in 90 g of water. To this solution was added 1 g of N-acryloylacrylamide, followed by 1 ml of a 1% aqueous solution of hydrogen peroxide and 5 ml of a 0.5% aqueous solution of ferrous sulfate. This mixture was polymerized at 40° C. for 5 hours to form a water-insoluble copolymer. The resulting copolymer gel was reduced to particles of 6-mesh or smaller size. A 20-g portion of the gel was worked up in the same manner as described in Example 3. On the basis of the ethanol concentration of the column effluent, the density of the immobilized yeast cells was estimated to be $4 \times 10^9$ cells per gram of the copolymer.

EXAMPLE 8

In 100 ml of water containing 0.1 g of sodium hydroxide was dispersed 15 g (on a dry basis) of corn starch. After the addition of 0.02 g of epichlorohydrin, this dispersion was reacted at 50° C. for 10 hours. Thereafter, the reaction system was adjusted to pH 7 with hydrochloric acid and then diluted with water to a total weight of 150 g. Then, 15 g of 2-acrylamido-2-methyl-propanesulfonic acid, 3 ml of 1N nitric acid, and 0.4 g of ammonium cerium nitrate were added thereto, and this mixture was reacted at 30° C. for 5 hours. The resulting gel was reduced to particles of 6-mesh or smaller size. A 10-g portion of the gel was placed in a 200-ml Erlenmeyer flask, washed three times with 50-ml portions of purified water, and then sterilized.

Next, 100 ml of a nutrient medium (pH 7) containing 3% of ammonium fumarate, 0.2% of dipotassium phosphate, 0.025% of magnesium sulfate, 4% of corn steep liquor, and 0.05% of calcium carbonate was inoculated with *Escherichia coli* and then shaken at 35° C. for 24 hours. Thereafter, 50 ml of the resulting culture of *Eschericia coli* and 50 ml of a fresh nutrient medium were added to the aforesaid gel-containing flask, which was shaken at 35° C. for 24 hours. After removal of the supernatant, the gel was washed three times with 50-ml portions of sterilized water. Then, 100 ml of a fresh nutrient medium was added to the gel-containing flask, which was shaken at 35° C. As a result, aspartic acid was produced at a rate of 872 μmol/hr/g of gel.

What is claimed is:

1. Method of immobilizing microorganisms which comprises the steps of bringing a suspension of living cells of a microorganism into contact with water-insoluble copolymer gel particles containing 10 to 99% by weight of structural units derived from 2-Acrylamidoethanesulfonic acid or a derivative thereof and a remainder of either a crosslinkable vinyl monomer having two or more ethylenic double bonds or of such a crosslinkable vinyl monomer having two or more ethylenic double bonds and a monoethylenic monomer, to cause the microorganism to become adsorbed on the copolymer gel particles, and bringing the water-insoluble copolymer gel particles having the microorganism adsorbed thereon into contact with a nutrient medium for the cultivation of the microorganism to increase the number of cells present on the copolymer gel particles.

2. Method of claim 1, wherein the water-insoluble copolymer in the copolymer gel particles is a copolymer of 2-acrylamidoethanesulfonic acid or a derivative thereof and a crosslinkable vinyl monomer having two or more ethylenic double bonds.

3. Method of claim 2, wherein the structural units derived from 2-acrylamidoethanesulfonic acid or a derivative thereof are structural units derived from one or more compounds selected from the group consisting of 2-acrylamidoethanesulfonic acid, 2-acrylamidopropanesulfonic acid, 2-acrylamido-2-methylpropanesulfonic acid, and alkali metal or alkaline earth metal salts thereof, and the crosslinkable vinyl monomer is selected from the group consisting of N,N'-methylenebisacrylamide, N,N'-propylene-bisacrylamide, N-acryloylacrylamide, diacrylamido dimethyl ether, 1,2-diacrylamido ethylene glycol, ethyleneureabisacrylamide, 1,3,5-triacryl-hexahydro-S-triazine, and mixtures thereof.

4. Method of claim 1, wherein the water-insoluble copolymer in the copolymer gel particles is a copolymer of 2-acrylamidoethanesulfonic acid or a derivative thereof, a crosslinkable vinyl monomer having two or more ethylenic double bonds, and a monoethylenic monomer.

5. Method of claim 4, wherein the structural units derived from 2-acrylamidoethanesulfonic acid or a derivative thereof are structural units derived from one or more compounds selected from the group consisting of 2-acrylamidoethanesulfonic acid, 2-acrylamidopropanesulfonic acid, 2-acrylamido-2-methylproponesulfonic acid, and alkali metal or alkaline earth metal salts thereof, the crosslinkable vinyl monomer is selected from the group consisting of N,N'-methylenebisacrylamide, N,N'-propylene-bisacrylamide, N-acryloylacrylamide, diacrylamido dimethyl ether, 1,2-diacrylamido ethylene glycol, ethyleneureabisacrylamide, 1,3,5-triacryl-hexahydro-S-triazine, and mixtures thereof, and the monoethylenic monomer is selected from the group consisting of acrylic acid, methacrylic acid, acrylamide, and derivatives thereof; styrene, alkyl-substituted styrenes, acrylonitrile, methacrylonitrile, vinyl ethers, N-vinylpyrrolidone, vinyl acetate, maleic acid, and maleic anhydride; and mixtures thereof.

6. Method of claim 1, wherein the water-insoluble copolymer gel particles contain 20 to 80% by weight of structural units derived from 2-acrylamidoethanesulfonic acid or a derivative thereof.

7. Method of claim 1, which further includes the step of swelling the water-insoluble copolymer gel particles in water prior to contact of a suspension of living cells of a microorganism with the water-insoluble copolymer gel particles.

8. Method of immobilizing microorganisms which comprises the steps of bringing a suspension of living cells of a microorganism into contact with water-insoluble copolymer gel particles containg 10 to 99% by weight of structural units derived from 2-acrylamidoethanesulfonic acid or a derivative thereof and a remainder of a natural or synthetic high-molecular compound, the copolymer in said copolymer gel particles constituting a graft polymer obtained by the graft polymerization of 2-acrylamidoethanesulfonic acid or a derivative thereof on the natural or synthetic high-molecular compound, the structural units derived from 2-acrylamidoethanesulfonic acid or a derivative thereof being structural units derived from one or more compounds selected from the group consisting of 2-acrylamidoethanesulfonic acid, 2-acrylamidopropanesulfonic acid, 2-acrylamido-2-methyl-propanesulfonic acid, and alkali metal or alkaline earth metal salts thereof, to cause the microorganism to become adsorbed on the copolymer gel particles, and bringing the water-insoluble copolymer gel particles having the microorganism adsorbed thereon into contact with a nutrient medium for the cultivation of the microorganism to increase the number of cells present on the copolymer gel particles.

9. Method of claim 8, wherein the water-insoluble copolymer gel particles contain 20 to 80% by weight of structural units derived from 2-acrylamidoethanesulfonic acid or a derivative thereof.

10. Method of claim 8, which further includes the step of swelling the water-insoluble copolymer gel particles in water prior to contact of a suspension of living cells of a microorganism with the water-insoluble copolymer gel particles.

* * * * *